United States Patent
Svendsen et al.

(10) Patent No.: US 6,221,821 B1
(45) Date of Patent: Apr. 24, 2001

(54) HALOPEROXIDASES WITH ALTERED PH PROFILES

(75) Inventors: Allan Svendsen, Birkerød; Louise Jørgensen, Hørsholm, both of (DK)

(73) Assignee: Novozymes A/S Patents, Bagsvaerd (DK)

( * ) Notice: Subject to any disclaimer, the term of this patent is extended or adjusted under 35 U.S.C. 154(b) by 0 days.

(21) Appl. No.: 09/271,778

(22) Filed: Mar. 18, 1999

Related U.S. Application Data

(60) Provisional application No. 60/079,228, filed on Mar. 24, 1998.

(30) Foreign Application Priority Data

Mar. 18, 1998 (DK) .............................................. 1998 00374

(51) Int. Cl.$^7$ ............................... C12N 9/08; C12N 1/20; C12N 15/00; C07H 21/04

(52) U.S. Cl. ...................... 510/226; 435/192; 435/252.3; 435/320.1; 536/23.2

(58) Field of Search .................................. 435/192, 252.3, 435/320.1; 536/23.2; 510/226

(56) References Cited

FOREIGN PATENT DOCUMENTS

| WO 93/24618 | 12/1993 | (WO) . |
| WO 95/10602 | 4/1995 | (WO) . |
| WO 95/27009 | 10/1995 | (WO) . |
| WO 97/04102 | 2/1997 | (WO) . |
| WO 98/10060 | 3/1998 | (WO) . |

OTHER PUBLICATIONS

Chem. Abst. vol. 124 No. 7; Abst. No. 80667q PNAS (1996).

Chem. Abst. vol. 123 No. 13; Abst. No. 163839c Eur. J. Biochem. (1995).

*Primary Examiner*—Tekchand Saidha
(74) *Attorney, Agent, or Firm*—Elias J. Lambiris, Esq.

(57) ABSTRACT

Variants of a parent vanadium-containing haloperoxidase, which variant has haloperoxidase activity and an altered pH optimum and comprises a mutation in a position corresponding to at least one of the following positions: R490A, L, I, Q, M, E, D; A399G; F397N, Y, E, Q; P395A, S; R360A, L, I, Q, M, E, D; K353Q, M; S402A, T, V, S; D292L; A501S; W350F, Y; V495A, T, V, S; K394 A, L, I, Q, M, E, D; wherein the parent haloperoxidase has the amino acid sequence given in SEQ ID No. 1, or the parent haloperoxidase has an amino acid sequence which is at least 80% homologous to SEQ ID No. 1.

16 Claims, No Drawings

HALOPEROXIDASES WITH ALTERED PH PROFILES

CROSS-REFERENCE TO RELATED APPLICATIONS

This application claims priority under 35 U.S.C. 119 of Danish application PA 1998 00374 filed Mar. 18, 1998, and of U.S. provisional application 60/079,228 filed Mar. 24, 1998, the contents of which are fully incorporated herein by reference.

FIELD OF THE INVENTION

The present invention relates to haloperoxidase variants with an altered pH optimum compared to the wild type.

BACKGROUND OF THE INVENTION

Haloperoxidases form a class of enzymes which are able to oxidize halides (X=Cl-, Br-, or I-) in the presence of hydrogen peroxide to the corresponding hypohalous acid (HOX) according to:

$$H_2O_2 + X- + H+ \rightarrow H_2O + HOX$$

If a convenient nucleophilic acceptor is present, a reaction will occur with HOX whereby a diversity of halogenated reaction products may be formed.

A chloride peroxidase (EC 1.11.1.10) is an enzyme capable of oxidizing chloride, bromide and iodide ions with the consumption of $H_2O_2$.

A bromide peroxidase is an enzyme capable of oxidizing bromide and iodide ions with the consumption of $H_2O_2$.

A iodide peroxidase (EC 1.11.1.8) is an enzyme capable of oxidizing iodide ions with the consumption of $H_2O_2$.

Vanadium haloperoxidases are different from other haloperoxidases in that the prosthetic group in theses enzymes have structural features similar to vanadate (vanadium V), whereas the other haloperoxidases are hemeperoxidases.

Haloperoxidases have been isolated from various organisms: mammals, marine animals, plants, algae, a lichen, fungi and bacteria (for reference see *Biochimica et Biophysica Acta* 1161, 1993, pp. 249–256). It is generally accepted that haloperoxidases are the enzymes responsible for the formation of halogenated compounds in nature, although other enzymes may be involved.

The amino acid sequence (SEQ No. 1) for the vanadium-containing chloroperoxidase from the fungus *Curvularia inaequalis* has been published (see SWISS-PROT:P49053).

The amino acid sequence (SEQ No. 2) for the vanadium-containing chloroperoxidase from the fungus Curvularia verruculosa has been published (see WO 97/04102).

The X-ray structure of the vanadium-containing chloroperoxidase from the fungus Curvularia inaequalis has been published (Proc. Natl. Acad. Sci. U.S.A., 93(1), 1996, 392–396; and pdblvnc.ent).

Haloperoxidases are of current interest because of their broad range of potential industrial uses. For example, haloperoxidases have been proposed for use as an anti-microbial agent.

BRIEF DISCLOSURE OF THE INVENTION

The present invention relates to vanadium-containing haloperoxidase variants with an altered pH optimum compared to the parent haloperoxidase, so in particular the present invention deals with:

A variant of a parent vanadium-containing haloperoxidase, which variant has haloperoxidase activity and an altered pH optimum and comprises a mutation in a position corresponding to at least one of the following positions:
R490A, L, I, Q, M, E, D;
A399G;
F397N, Y, E, Q;
P395A, S;
R360A, L, I, Q, M, E ,D;
K353Q, M;
S402A, T, V, S;
D292L;
A501S;
W350F, Y;
V495A, T, V, S;
K394A, L, I, Q, M, E, D;
wherein the parent haloperoxidase has the amino acid sequence given in SEQ ID No. 1 or the parent haloperoxidase has an amino acid sequence which is at least 80% homologous to SEQ ID No. 1.

DETAILED DISCLOSURE OF THE INVENTION

Homologous vanadium-containing haloperoxidases

A number of vanadium-containing haloperoxidases produced by different fungi are homologous on the amino acid level.

An alignment of the *Curvularia inaequalis* and the *Curvularia verruculosa* haloperoxidases was performed. The alignment uses the haloperoxidase amino acid sequence obtained from the 3D structure file of *C. inaequalis* (Brookhaven databank file pdblvnc.ent).

When using the homology percent obtained from UWGCG program using the GAP program with the default parameters (penalties: gap weight=3.0, length weight=0.1; WISCONSIN PACKAGE Version 8.1-UNIX, August 1995, Genetics Computer Group, 575 Science Drive, Madison, Wis., U.S.A. 53711) the following homology was found: *Curvularia inaequalis* vanadium-containing haloperoxidase comprising the amino acid sequence shown in SEQ ID No. 1: 100%; *Curvularia verruculosa* vanadium-containing haloperoxidase comprising the amino acid sequence shown in SEQ ID No. 2: 96%.

In the present context, "derived from" is intended not only to indicate a vanadium-containing haloperoxidase produced or producible by a strain of the organism in question, but also a vanadium-containing haloperoxidase encoded by a DNA sequence isolated from such strain and produced in a host organism containing said DNA sequence. Finally, the term is intended to indicate a vanadium-containing haloperoxidase which is encoded by a DNA sequence of synthetic and/or cDNA origin and which has the identifying characteristics of the vanadium-containing haloperoxidase in question.

Variants With Altered pH Optimum

The desired pH optimum of a vanadium-containing haloperoxidase depends on which application is of interest, e.g., if the vanadium-containing haloperoxidase is to be used for denim bleaching the preferred pH optimum will be around pH 5–8, whereas if the vanadium-containing haloperoxidase is to be used for washing purposes the preferred pH optimum will be around pH 8–10.

It is possible to alter the pH optimum of a parent vanadium-containing haloperoxidase wherein said variant is the result of a mutation, i.e. one or more amino acid residues have been deleted from, replaced or added to the parent vanadium-containing haloperoxidase. By introducing charge changes in the neighbourhood of the active site residues, the pKa of the residue of interest can be changed in order to accomodate an altered activity profile of the haloperoxidase in question.

It is a common belief that by introducing more negative charged residues close to the His (the active site of the haloperoxidase), its pKa is elevated and it will thus be able to act in catalysis at a higher pH than previously. The active site His will, by introducing more positive charged residues close to His, alter its pKa to a lower pKa than previously and thus be able to act in catalysis at a lower pH than previously.

The increase in pKa can also be obtained by decreasing the solvent accessibility of the active site (His). The decrease in pKa can also be obtained by increasing the solvent accessibility of the active site (His).

But according to the present invention it is found that of most importance is that the residues are within 10 Å around His 496 and His 404. These residues are: 46–48, 193, 257, 259–265, 267–269, 285–294, 297–304, 307, 242, 245–346, 349–350, 353, 358–363, 365, 378, 380–384, 393–412, 441, 443, 482–502, 507, 551–557. Changes within this region are found to alter the pH dependent activity or change the pH-optimum of the enzyme. Residues can in this way be mutated in e.g. the *Curvularia inaequalis* haloperoxidase. Homologous structures which are assumed to have similar structure can be modelbuild (see Example 1) and regions of interest found in the same way.

Preferred positions for mutations are the following:
R490A, L, I, Q, M, E, D;
A399G;
F397N, Y, E, Q;
P395A, S;
R360A, L, I, Q, M, E, D;
K353Q, M;
S402A, T, V, S;
D292L, E;
A501S;
W350F, Y;
V495A, T, V, S;
K394 A, L, I, Q, M, E, D;
wherein the parent haloperoxidase has the amino acid sequence given in SEQ ID No. 1, or the homologous positions in a parent haloperoxidase which has an amino acid sequence which is at least 80% homologous to SEQ ID No. 1, or the homologous positions in a parent haloperoxidase which has an amino acid sequence which is at least 85% homologous to SEQ ID No. 1, or the homologous positions in a parent haloperoxidase which has an amino acid sequence which is at least 90% homologous to SEQ ID No. 1, or the homologous positions in a parent haloperoxidase which has an amino acid sequence which is at least 95% homologous to SEQ ID No. 1, or the homologous positions in a parent haloperoxidase which has an amino acid sequence which is at least 96% homologous to SEQ ID No. 1, or the homologous positions in a parent haloperoxidase which has an amino acid sequence which is at least 97% homologous to SEQ ID No. 1, or the homologous positions in a parent haloperoxidase which has an amino acid sequence which is at least 98% homologous to SEQ ID No. 1, or the homologous positions in a parent haloperoxidase which has an amino acid sequence which is at least 99% homologous to SEQ ID No. 1.

In particular the following mutations are preferred:
R487A, L, I, Q, M, E, D;
A396G;
F394N, Y, E, Q;
P392A, S;
R357A, L, I, Q, M, E, D;
K350Q, M;
S399A, T, V, S;
D289L, E;
A498S;
W347F, Y;
V492A, T, V, S;
K391A, L, I, Q, M, E, D;
wherein the parent haloperoxidase has the amino acid sequence given in SEQ ID No. 2.

In a preferred embodiment two or more amino acid residues may be substituted as follows:
R490A+D292L;
R490A+D292E;
R490L+D292L;
R490L+D292E;
R490I+D292L;
R490I+D292E;
R490Q+D292L;
R490Q+D292E;
R490M+D292L;
R490M+D292E;
R490E+D292L;
R490E+D292E;
R490D+D292L;
R490D+D292E;
wherein the parent haloperoxidase has the amino acid sequence given in SEQ ID No. 1, or the homologous positions in a parent haloperoxidase which has an amino acid sequence which is at least 80% homologous to SEQ ID No. 1, or the homologous positions in a parent haloperoxidase which has an amino acid sequence which is at least 85% homologous to SEQ ID No. 1, or the homologous positions in a parent haloperoxidase which has an amino acid sequence which is at least 90% homologous to SEQ ID No. 1, or the homologous positions in a parent haloperoxidase which has an amino acid sequence which is at least 95% homologous to SEQ ID No. 1, or the homologous positions in a parent haloperoxidase which has an amino acid sequence which is at least 96% homologous to SEQ ID No. 1, or the homologous positions in a parent haloperoxidase which has an amino acid sequence which is at least 97% homologous to SEQ ID No. 1, or the homologous positions in a parent haloperoxidase which has an amino acid sequence which is at least 98% homologous to SEQ ID No. 1, or the homologous positions in a parent haloperoxidase which has an amino acid sequence which is at least 99% homologous to SEQ ID No. 1.

In a preferred embodiment two or more amino acid residues may be substituted as follows:
R487A+D289L;
R487A+D289E;
R487L+D289L;
R487L+D289E;
R487I+D289L;
R487I+D289E;
R487Q+D289L;
R487Q+D289E;
R487M+D289L;
R487M+D289E;
R487E+D289L;
R487E+D289E;
R487D+D289L;
R487D+D289E;
wherein the parent haloperoxidase has the amino acid sequence given in SEQ ID No. 2.

Methods of Preparing Vanadium-Containing Haloperoxidase Variants

Several methods for introducing mutations into genes are known in the art. After a brief discussion of the cloning of haloperoxidase-encoding DNA sequences, methods for generating mutations at specific sites within the haloperoxidase-encoding sequence will be discussed.

Cloning a DNA Sequence Encoding a Vanadium-Containing Haloperoxidase

The DNA sequence encoding a parent vanadium-containing haloperoxidase may be isolated from any cell or microorganism producing the haloperoxidase in question, using various methods well known in the art. First, a genomic DNA and/or cDNA library should be constructed using chromosomal DNA or messenger RNA from the organism that produces the haloperoxidase to be studied. Then, if the amino acid sequence of the haloperoxidase is known, homologous, labelled oligonucleotide probes may be synthesized and used to identify haloperoxidase-encoding clones from a genomic library prepared from the organism in question. Alternatively, a labelled oligonucleotide probe containing sequences homologous to a known haloperoxidase gene could be used as a probe to identify haloperoxidase-encoding clones, using hybridization and washing conditions of lower stringency.

A method for identifying haloperoxidase-encoding clones involves inserting cDNA into an expression vector, such as a plasmid, transforming haloperoxidase-negative fungi with the resulting cDNA library, and then plating the transformed fungi onto agar containing a substrate for the haloperoxidase, thereby allowing clones expressing the haloperoxidase to be identified.

Alternatively, the DNA sequence encoding the enzyme may be prepared synthetically by established standard methods, e.g. the phosphoroamidite method. In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers.

Site-Directed Mutagenesis

Once a haloperoxidase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the haloperoxidase-encoding sequence, is created in a vector carrying the haloperoxidase gene. Then the synthetic nucleotide, bearing the desired mutation, is annealed to a homologous portion of the single-stranded DNA. The remaining gap is then filled in with T7 DNA polymerase and the construct is ligated using T4 ligase (Morinaga method—see Biotechnology, 2, 1984, pp. 626–639). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method of introducing mutations into haloperoxidase-encoding DNA sequences is the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random mutagenesis

The random mutagenesis of a DNA sequence encoding a parent haloperoxidase may conveniently be performed by use of any method known in the art.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents.

The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the haloperoxidase enzyme by any published technique, using e.g. PCR, LCR or any DNA polymerase and ligase.

When PCR-generated mutagenesis is used, either a chemically treated or non-treated gene encoding a parent haloperoxidase enzyme is subjected to PCR under conditions that increase the misincorporation of nucleotides (Deshler 1992; Leung et al., Technique, Vol.1, 1989, pp. 11–15).

A mutator strain of *E. coli* (Fowler et al., Molec. Gen. Genet., 133, 1974, pp. 179–191), *S. cereviseae* or any other microbial organism may be used for the random mutagenesis of the DNA encoding the haloperoxidase enzyme by e.g. transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or cDNA library prepared from an organism expressing the parent haloperoxidase enzyme. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to the expression step or the screening step being performed. Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenizing agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are fungal hosts such as Aspergillus niger or Aspergillus oryzae.

The mutated DNA sequence may further comprise a DNA sequence encoding functions permitting expression of the mutated DNA sequence.

Localized Random Mutagenesis

The random mutagenesis may advantageously be localized to a part of the parent haloperoxidase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized random mutagenesis is conveniently performed by use of PCR-generated mutagenesis techniques as described above or any other suitable technique known in the art.

Alternatively, the DNA sequence encoding the part of the DNA sequence to be modified may be isolated, e.g. by being inserted into a suitable vector, and said part may subsequently be subjected to mutagenesis by use of any of the mutagenesis methods discussed above.

With respect to the screening step in the above-mentioned method of the invention, this may conveniently be performed by use of a filter assay based on the following principle:

A microorganism capable of expressing the mutated haloperoxidase enzyme of interest is incubated on a suitable medium and under suitable conditions for the enzyme to be secreted, the medium being provided with a double filter comprising a first protein-binding filter and on top of that a second filter exhibiting a low protein binding capability. The microorganism is located on the second filter. Subsequent to the incubation, the first filter comprising enzymes secreted from the microorganisms is separated from the second filter comprising the microorganisms. The first filter is subjected to screening for the desired enzymatic activity and the corresponding microbial colonies present on the second filter are identified.

The filter used for binding the enzymatic activity may be any protein binding filter e.g. nylon or nitrocellulose. The top filter carrying the colonies of the expression organism may be any filter that has no or low affinity for binding proteins e.g. cellulose acetate or Durapore™. The filter may be pretreated with any of the conditions to be used for screening or may be treated during the detection of enzymatic activity.

The enzymatic activity may be detected by a dye, fluorescence, precipitation, pH indicator, IR-absorbance or any other known technique for detection of enzymatic activity.

The detecting compound may be immobilized by any immobilizing agent, e.g., agarose, agar, gelatine, polyacrylamide, starch, filter paper, cloth; or any combination of immobilizing agents.

Expression of Haloperoxidase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding a haloperoxidase variant of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding a haloperoxidase variant of the invention, especially in a fungal host, are those derived from the gene encoding A. oryzae TAKA amylase, Rhizomucor miehei aspartic proteinase, A. niger neutral α-amylase, A. niger acid stable α-amylase, A. niger glucoamylase, Rhizomucor miehei lipase, A. oryzae alkaline protease, A. oryzae triose phosphate isomerase or A. nidulans acetamidase.

The expression vector of the invention may also comprise a suitable transcription terminator and, in eukaryotes, polyadenylation sequences operably connected to the DNA sequence encoding the haloperoxidase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene, the product of which complements a defect in the host cell, such as one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding a haloperoxidase variant, the promoter, terminator and other elements, respectively, and to insert them into suitable vectors containing the information necessary for replication, are well known to persons skilled in the art (cf., for instance, Sambrook et al. (1989)).

The cell of the invention, either comprising a DNA construct or an expression vector of the invention as defined above, is advantageously used as a host cell in the recombinant production of a haloperoxidase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a fungal cell.

The filamentous fungus may advantageously belong to a species of Aspergillus, e.g. *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing a haloperoxidase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the haloperoxidase variant of the invention. Suitable media are available from commercial suppliers or may be prepared according to published recipes (e.g. as described in catalogues of the American Type Culture Collection).

The haloperoxidase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Industrial Applications

The haloperoxidase of the invention may be incorporated into a detergent or cleaning composition comprising other enzyme types useful in detergent or cleaning compositions, preferably at least one further enzyme selected from the group consisting of proteases, amylases, cutinases, peroxidases, oxidases, laccases, cellulases, xylanases, and lipases. In particular, the haloperoxidase of the invention may be used for bleaching and for sanitation purposes.

When used for preservation of food, beverages, cosmetics such as lotions, creams, gels, ointments, soaps, shampoos, conditioners, antiperspirants, deodorants, mouth wash, contact lens products, enzyme formulations, or food ingredients, the haloperoxidase of the invention may be incorporated into the e.g. unpreserved food, beverages, cosmetics, contact lens products, food ingredients or anti-inflammatory product in an amount effective for killing or inhibiting growing of microbial cells.

Thus, the haloperoxidase used in the method of the invention may by useful as a disinfectant, e.g., in the treatment of acne, infections in the eye or the mouth, skin infections; in antiperspirants or deodorants; in foot bath salts; for cleaning end disinfection of contact lenses, hard surfaces, teeth (oral care), wounds, bruises and the like.

In general it is contemplated that the haloperoxidase of the present invention is useful for cleaning, disinfecting or inhibiting microbial growth on any hard surface. Examples of surfaces, which may advantageously be contacted with the composition of the invention are surfaces of process equipment used e.g. dairies, chemical or pharmaceutical process plants, water sanitation systems, paper pulp processing plants, water treatment plants, and cooling towers. The haloperoxidase of the invention should be used in an amount, which is effective for cleaning, disinfecting or inhibiting microbial growth on the surface in question.

Further, it is contemplated that the haloperoxidase of the invention can advantageously be used in a cleaning-in-place (C.I.P.) system for cleaning of process equipment of any kind.

The haloperoxidase of the invention may additionally be used for cleaning surfaces and cooking utensils in food processing plants and in any area in which food is prepared or served such as hospitals, nursing homes, restaurants, especially fast food restaurants, delicatessens and the like. It may also be used as an antimicrobial in food products and would be especially useful as a surface antimicrobial in cheeses, fruits and vegetables and food on salad bars.

It may also be used as a preservation agent or a disinfection agent in water based paints:

Conservation/Preservation of Paints

Conservation of paint products in cans has in the art been accomplished by adding non-enzymatic organic biocides to the paints. In the context of the invention paint is construed as a substance comprising a solid colouring matter dissolved or dispersed in a liquid vehicle such as water, organic solvent and/or oils, which when spread over a surface, dries to leave a thin coloured, decorative and/or protective coating. Typically isothiazoliones, such as 5-chlor-2-methyl-4-thia-zoli-3-on, has been added to the paint as biocides at dosages in the range of about 0.05–0.5% to inhibit/prevent microbial growth in the paint. The method of the invention can however suitably be applied in this field, thereby solving the problem of the ever present environmental bio-hazards of using toxic organic biocides by replacing these toxic biocides with environmentally compatible enzymes. Thus the invention provides a method for conservation of a paint comprising contacting said paint with a haloperoxidase variant according to the invention. Further the invention provides a paint composition comprising a haloperoxidase variant according to the invention.

The paint is preferably a water based paint, i.e. the solids of the paint is dispersed in an aqueous solution. The paint may contain 0–20% organic solvent, preferable 0–10%, e.g. 0–5%.

The enzyme may be added to the paint in an amount of 0.0001–100 mg active enzyme protein per liter paint, preferable 0.001–10 mg/liter, e.g. 0.01–1 mg/liter.

Hydrogen Peroxide Sources

According to the invention the hydrogen peroxide needed for the reaction with the haloperoxidase may be obtained in many different ways: It may be hydrogen peroxide or a hydrogen peroxide precursor, such as, e.g., percarbonate or perborate, or a peroxycarboxylic acid or a salt thereof, or it may be a hydrogen peroxide generating enzyme system, such as, e.g., an oxidase and its substrate. Useful oxidases may be, e.g., a glucose oxidase, a glycerol oxidase or an amino acid oxidase. An example of an amino acid oxidase is given in WO 94/25574.

It may be advantageous to use enzymatically generated hydrogen peroxide, since this source results in a relatively low concentration of hydrogen peroxide under the biologically relevant conditions. Low concentrations of hydrogen peroxide result in an increase in the rate of haloperoxidase-catalysed reaction.

According to the invention the hydrogen peroxide source needed for the reaction with the haloperoxidase may be added in a concentration corresponding to a hydrogen peroxide concentration in the range of from 0.01–1000 mM, preferably in the range of from 0.1–500 mM.

Halide Sources

According to the invention the halide source needed for the reaction with the haloperoxidase may be achieved in many different ways, e.g., by adding a halide salt: It may be sodium chloride, potassium chloride, sodium bromide, potassium bromide, sodium iodide, or potassium iodide.

The concentration of the halide source will typically correspond to 0.01–1000 mM, preferably in the range of from 0.1–500 mM.

The Composition

The composition comprising the haloperoxidase, the hydrogen peroxide source, and the halide source may be formulated as a solid or a liquid, in particular in the form of a non-dusting granulate, or a stabilised liquid.

When formulated as a solid all components may be mixed together, e.g., as a powder, a granulate or a gelled product.

When other than dry form compositions are used and even in that case, it is preferred to use a two part formulation system having the hydrogen peroxide separate from the other components.

The composition of the invention may further comprise auxiliary agents such as wetting agents, thickening agents, buffer, stabilisers, perfume, colourants, fillers and the like.

Useful wetting agents are surfactants, i.e., non-ionic, anionic, amphoteric or zwitterionic surfactants.

The composition of the invention may be a concentrated product or a ready-to-use product.

Haloperoxidase Activity

According to the present invention haloperoxidase activity may be measured as described in WO 97/04102, p. 13 l. 7–19.

The present invention is further illustrated in the following examples which are not in any way intended to limit the scope of the invention as claimed.

EXAMPLE 1

Homology building of the *Curvularia Verruculosa* Haloperoxidase 3D-Structure

Using sequence homology of *Curvularia ineaqualis* (CI) to other sequences, e.g., *Curvularia verruculosa,* CI-like 3 D-structures can be found.

In comparison with the *Curvularia ineaqualis,* used for elucidating the structure, *Curvularia verruculosa* differs in a number of residues. The model may be built using the INSIGHT and HOMOLOGY programs from Molecular Simulations Inc. The program substitutes the amino acids in the *Curvularia ineaqualis* with amino acids from *Curvularia verruculosa* in the homologous positions defined in the program as structurally conserved regions (SCR). The residues in between are built using the LOOP option with GENERATE. Using these steps a crude model may be obtained which gives information of spatial interactions.

The structure can be refined using the method described in the HOMOLOGY package.

EXAMPLE 2

Construction of Haloperoxidase Variants

For the construction of variants of the *Curvularia verruculosa* haloperoxidase enzyme the commercial kit, Chameleon double-stranded, site-directed mutagenesis kit, can be used according to the manufacturer's instructions.

The gene encoding the haloperoxidase enzyme in question is located on the plasmid pElo29. In accordance with the manufacturer's instructions, the ScaI site of the Ampicillin gene of pElo29 is changed to a MluI site by use of the primer 117996 (SEQ ID NO: 3). At the same time the desired mutation is introduced into the haloperoxidase gene by the addition of an appropriate primer comprising the desired mutation.

Construction of the plasmid pElo29

The plasmid pElo29 was built from the following fragments:

a) The 4.1 kb fragment from the vector pCiP (described in WO 93/34618) cut with BamHI and BglII.

b) The *Curvularia verruculosa* haloperoxidase gene amplified by PCR with Pwo polymerase using the plasmid pAJ014-1 (WO 97/04102) as template, and the primers 146063 and 146062 (SEQ ID NO: 4 and 5) introducing BamHI and BglII sites 5' and 3' respectively to the haloperoxidase gene.

Following ligation of the fragments a and b, the whole haloperoxidase gene were sequenced to ensure that no undesired mutations had been introduced during the PCR amplification.

Site-directed mutagenesis

Site directed mutagenesis as described above was used to construct plasmids harboring genes encoding variants of the haloperoxidase enzyme. The following primers were used:

The primer 147293 (SEQ ID NO: 6) was used to introduce D289L.

The primer 147295 (SEQ ID NO: 7) was used to introduce D289E.

The primer 139078 (SEQ ID NO: 8) was used to introduce R487E.

The primer 139085 (SEQ ID NO: 9) was used to introduce V492S.

The mutations were in each case verified by sequencing of the whole gene. The resulting plasmids were called pElo30, pElo31, pElo34 and pElo37 respectively.

Transformation of pElo30, pElo31, pElo34 and pElo37 into JaL 228

*Aspergillus oryzae* JaL 228 (WO 97/27221) is *Aspergillus oryzae* IFO 4177 deleted in the alkaline protease and the neutral metalloprotease I. This strain was transformed with pElo30, pElo31, pElo34 and pElo37 using the plasmid pToC90 (WO 91/17243) carrying the amdS gene as cotransformant. Selection of transformants were performed using acetamide as described in patent EP 0 531 372 B1. Transformants were spore reisolated twice. Spores from second reisolation of each transformant were tested for haloperoxidase production in small scale fermentations (shake flasks and microtiterdishes).

Fermentation of *Curvularia verruculosa* haloperoxidase variants in *Aspergillus oryzae*

Isolates from above were fermented in a tank medium comprised of 12 g of sucrose, 20 g of 50% yeast extract, 2 g of MgSO4*7H2O, 2 g of KH2PO4, 3 g of K2SO4, 4 g of citric acid, 1 ml of pluronic, 182 mg of V2O5, and 0.5 ml of trace metals solution¤ per liter, and fed during the course of the fermentation with a medium comprised of 250 g 80% maltose solution, 20 g of 50% yeast extract, 5 g of citric acid, 5 ml of pluronic, 182 mg of V2O5, and 0.5 ml of trace metals solution¤ per liter. The fermentation broth were harvested after 5 days of fermentation at 34oC, pH above 6.0.

¤ Trace metals solution: 14.3 g of ZnSO4*7H2O, 2.5 g of CuSO4*5H2O, 0.5 g of NiCl2*6H2O, 13.8 g of FeSO4*7H2O, 8.5 g of MnSO4*H2O, and 3.0 g of citric acid per liter.

<u>Sequence list</u>

SEQ ID NO 3: Primer 117996; changed nucleotides are underlined and leads to elimination of the ScaI site, and introduction of the MluI site in pElo29:

Sequence list

5'-GA ATG ACT TGG TTG A<u>CGCGT</u> CAC CAG TCA C-3'

SEQ ID NO 4: Primer 146063; PCR primer for amplification of the *Curvularia verruculosa* haloperoxidase gene. Underlined nucleotides introduces the BamHI site:

5'-CGC <u>GGATCC</u>TCT ATA TAC ACA ACT GG-3'

SEQ ID NO 5: Primer 146062; PCR primer for amplification of the *Curvularia verruculosa* haloperoxidase gene. Underlined nucleotides introduces the BglII site:

5'-GA<u>AGATCT</u>C GAG TTA ATT AAT CAC TGG-3'

SEQ ID NO 6: Primer 147293; Underlined nucleotides introduces the D289L mutation in the haloperoxidase enzyme in question:

5'-GG TCT GTA TTG GGC CTA C<u>CT</u>TGG GTC AAA CC-3'

SEQ ID NO 7: Primer 147295; Underlined nucleotides introduces the D289E mutation in the haloperoxidase enzyme in question:

5'-GG TCT GTA TTG GGC CTA C<u>GA</u>GGG GTC AAA CC-3'

SEQ ID NO 8: Primer 139078; Underlined nucleotides introduces the R487E mutation in the haloperoxidase enzyme in question:

5'-CG CCA TTT CT<u>GAGA</u> TCT TCC TGG GC-3'

SEQ ID NO 9: Primer 139085; Underlined nucleotides introduces the V492S mutation in the haloperoxidase enzyme in question:

5'-GC ATC TTC CTC GGC<u>AGC</u> CAC TGG CGA TTC GAT GCC G-3'

EXAMPLE 3
pH-Curves of Various Haloperoxidase Variants

The haloperoxidase variants (derived from *Curvularia verruculosa*) were made as described in Example 2.

Experimental

Phenol Red Assay for pH-Profile Determination

In 96 well microtiter plates 100 µl 0.008% phenol red in 60 mM Britton-Robinson buffer, pH 4–8.5. To these solutions were added 40 µl 0.5 M KBr and 50 µl diluted enzyme solution containing 1 mM of ortho-vanadate. The reaction was started by adding 10 µl 0.3% hydrogen peroxide and the kinetic was measured over 5 minutes at 595 nm.

Results

Activity was taken relative to the highest value for each enzyme:

It can be seen from the Table that the wild type has a pH optimum at pH 7.0; the variant D289E and R487E and V492S have a pH optimum at 6.0; and the variant D289L has a pH optimum at pH 7.5.

EXAMPLE 4
pH-Curve of Purified Haloperoxidase Variant (V492S)

The haloperoxidase variant (V492S) described above and the *Curvularia verruculosa* wild type were purified and tested with Chicago Skye Blue:

Purification of Haloperoxidases

Fermentation broth containing haloperoxidase activity was filtered GF/F (Whatmann) and 0.22 µm (GS, Millipore) before concentrating on the Filtron (cut off 10 kDa). The pH was adjusted to pH 7.5 and the sample loaded onto a Q-Sepharose column (Pharmacia) equilibrated in 50 mM Tris-HCl, pH 7.5. The haloperoxidase was eluted in a linear gradient of 0–1 M NaCl in 50 mM Tris-HCl, pH 7.5. Haloperoxidase containing fractions were concentrated on an Amicon cell (YM10 membrane) and loaded onto MonoQ-column (Pharmicia) equilibrated in 50 mM Tris-HCl, pH 8.5 and eluted in a linear gradient of 0–1 M NaCl in 50 mM Tris-HCl. Haloperoxidase containing fractions were pooled and further purified on a Superdex75 column 16/60 (Pharmacia) equilibrated in 50 mM sodium acetate, 0.1 M NaCl, pH 5.5.

Experimental

In 96 Well Microtiter Plates 100 µl 60 mM Britton-Robinson pH 4–8+50 µl enzyme solution+25 µl 0.4 M NaCl+25 µl Chicago Skye Blue diluted in water to OD610=5. The reaction was started by adding 10 µl of 2 mM H2O2. The activity was taken as the linear decrease in adsorption at 595 nm.

| pH | Relative activities: wt | V492S |
|---|---|---|
| 4 | 0 | 0.11 |
| 4.5 | 0 | 0.62 |
| 5 | 0.25 | 0.93 |
| 5.5 | 1 | 1 |
| 6 | 0.89 | 0.70 |
| 6.5 | 0.41 | 0.34 |
| 7 | 0.11 | 0.08 |
| 7.5 | 0.02 | 0.02 |
| 8 | 0 | 0.01 |

CONCLUSION

V492S clearly exhibits increased activity in the low pH range compared to the wt enzyme.

| Variant | pH 4.0 | pH 4.5 | pH 5.0 | pH 5.5 | pH 6.0 | pH 6.5 | pH 7.0 | pH 7.5 | pH 8.0 | pH 8.5 |
|---|---|---|---|---|---|---|---|---|---|---|
| rCv wt | 0 | 0.01 | 0.14 | n.d. | 0.16 | 0.34 | 1.00 | 0.89 | 0.51 | 0.18 |
| D289E | 0.01 | 0.10 | 0.63 | 0.98 | 1.00 | 0.85 | 0.52 | 0.25 | 0.11 | 0.03 |
| D289L | 0 | 0 | 0 | 0.01 | 0.12 | 0.39 | 0.97 | 1.00 | 0.55 | 0.14 |
| R487E | 0 | 0 | 0.31 | 0.84 | 1.00 | 0.83 | 0.48 | 0.20 | 0.09 | 0.03 |
| V492S | 0 | 0.01 | 0.53 | 0.95 | 1.00 | 0.98 | 0.77 | 0.42 | 0.19 | 0.06 |

What is claimed is:

1. A variant having haloperoxidase activity, an altered pH optimum compared with a haloperoxidase, an amino acid sequence that differs from the amino acid sequence of the haloperoxidase, wherein the amino acid sequence of the haloperoxidase is at least 80% homologous with the haloperoxidase of SEQ ID NO:1 and the difference between the amino acid sequence of the variant and the amino acid sequence of the haloperoxidase comprises:

(a) a different amino acid at position 292 wherein the different amino acid is L or E;

(b) a different amino acid at position 350 wherein the different amino acid is F or Y;

(c) a different amino acid at position 353 wherein the different amino acid is Q or M;

(d) a different amino acid at position 360 selected from the group consisting of A, L, I, Q, M, E and D;

(e) a different amino acid at position 394 selected from the group consisting of A, L, I, Q, M, E and D;

(f) a different amino acid at position 395 wherein the different amino acid is A or S;

(g) a different amino acid at position 397 selected from the group consisting of N, Y, E, and Q;

(h) a different amino acid at position 399 wherein the different amino acid is G;

(i) a different amino acid at position 402 selected from the group consisting of A, T, and V;

(j) a different amino acid at position 490 selected from the group consisting of A, L, I, Q, M, E, and D;

(k) a different amino acid at position 495 selected from the group consisting of A, T, and S; and/or (l) a different amino acid at position 501 wherein the different amino acid is S, wherein each position corresponds to the position of the amino acid sequence of the haloperoxidase of SEQ ID NO:1.

2. The variant of claim 1, wherein the difference between the amino acid sequence of the variant and the amino acid sequence of the haloperoxidase comprises a different amino acid at position 487 selected from the group consisting of E, D, Q and A.

3. The variant of claim 1, wherein the difference between the amino acid sequence of the variant and the amino acid sequence of the haloperoxidase comprises a different amino acid at position 289 wherein the different amino acid is E or L.

4. The variant of claim 1, wherein the difference between the amino acid sequence of the variant and the amino acid sequence of the haloperoxidase comprises a different amino acid at position 492 is S or T.

5. The variant of claim 1, wherein the difference between the amino acid sequence of the variant and the amino acid sequence of the haloperoxidase comprises a different amino acid at position 289 wherein the different amino acid is L and a different amino acid at position 487 wherein the different amino acid is E.

6. The variant of claim 1, wherein the difference between the amino acid sequence of the variant and the amino acid sequence of the haloperoxidase comprises a different amino acid at position 289 wherein the different amino acid is L, a different amino acid at position 487 wherein the different amino acid is E, and a different amino acid at position 492 wherein the different amino acid is T.

7. The variant of claim 1, wherein the haloperoxidase is a Curvularia haloperoxidase.

8. The variant of claim 7, wherein the haloperoxidase is a *Curvularia inaequalis* haloperoxidase.

9. The variant of claim 7, wherein the haloperoxidase is *Curvularia verruculosa* haloperoxidase.

10. The variant of claim 7, wherein the haloperoxidase has an amino acid sequence of SEQ ID NO:1.

11. The variant of claim 7, wherein the haloperoxidase has an amino acid sequence of SEQ ID NO:2.

12. A detergent additive comprising a variant of claim 1 in the form of a non-dusting gratulate, a stabilised liquid or a protected enzyme.

13. A detergent additive of claim 12, further comprising a protease, lipase, amylase, and/or cellulase.

14. A detergent composition comprising a variant of claim 1 and a surfactant.

15. A detergent composition of claim 14, further comprising a protease, lipase, amylase and/or cellulase.

16. A paint comprising a variant of claim 1.

* * * * *

SEQUENCE LISTING

<160> NUMBER OF SEQ ID NOS: 9

<210> SEQ ID NO 1
<211> LENGTH: 609
<212> TYPE: PRT
<213> ORGANISM: Curvularia inaequalis

<400> SEQUENCE: 1

```
Met Gly Ser Val Thr Pro Ile Pro Leu Pro Lys Ile Asp Glu Pro Glu
 1               5                  10                  15

Glu Tyr Asn Thr Asn Tyr Ile Leu Phe Trp Asn His Val Gly Leu Glu
            20                  25                  30

Leu Asn Arg Val Thr His Thr Val Gly Gly Pro Leu Thr Gly Pro Pro
        35                  40                  45

Leu Ser Ala Arg Ala Leu Gly Met Leu His Leu Ala Ile His Asp Ala
    50                  55                  60

Tyr Phe Ser Ile Cys Pro Pro Thr Asp Phe Thr Thr Phe Leu Ser Pro
65                  70                  75                  80

Asp Thr Glu Asn Ala Ala Tyr Arg Leu Pro Ser Pro Asn Gly Ala Asn
                85                  90                  95

Asp Ala Arg Gln Ala Val Ala Gly Ala Ala Leu Lys Met Leu Ser Ser
            100                 105                 110

Leu Tyr Met Lys Pro Val Glu Gln Pro Asn Pro Asn Pro Gly Ala Asn
        115                 120                 125

Ile Ser Asp Asn Ala Tyr Ala Gln Leu Gly Leu Val Leu Asp Arg Ser
    130                 135                 140

Val Leu Glu Ala Pro Gly Gly Val Asp Arg Glu Ser Ala Ser Phe Met
145                 150                 155                 160

Phe Gly Glu Asp Val Ala Asp Val Phe Phe Ala Leu Leu Asn Asp Pro
                165                 170                 175

Arg Gly Ala Ser Gln Glu Gly Tyr His Pro Thr Pro Gly Arg Tyr Lys
            180                 185                 190

Phe Asp Asp Glu Pro Thr His Pro Val Val Leu Ile Pro Val Asp Pro
        195                 200                 205

Asn Asn Pro Asn Gly Pro Lys Met Pro Phe Arg Gln Tyr His Ala Pro
    210                 215                 220

Phe Tyr Gly Lys Thr Thr Lys Arg Phe Ala Thr Gln Ser Glu His Phe
225                 230                 235                 240

Leu Ala Asp Pro Pro Gly Leu Arg Ser Asn Ala Asp Glu Thr Ala Glu
                245                 250                 255

Tyr Asp Asp Ala Val Arg Val Ala Ile Ala Met Gly Gly Ala Gln Ala
            260                 265                 270

Leu Asn Ser Thr Lys Arg Ser Pro Trp Gln Thr Ala Gln Gly Leu Tyr
        275                 280                 285

Trp Ala Tyr Asp Gly Ser Asn Leu Ile Gly Thr Pro Pro Arg Phe Tyr
    290                 295                 300

Asn Gln Ile Val Arg Arg Ile Ala Val Thr Tyr Lys Lys Glu Glu Asp
305                 310                 315                 320

Leu Ala Asn Ser Glu Val Asn Asn Ala Asp Phe Ala Arg Leu Phe Ala
                325                 330                 335

Leu Val Asp Val Ala Cys Thr Asp Ala Gly Ile Phe Ser Trp Lys Glu
            340                 345                 350

Lys Trp Glu Phe Glu Phe Trp Arg Pro Leu Ser Gly Val Arg Asp Asp
```

```
                355              360               365
Gly Arg Pro Asp His Gly Asp Pro Phe Trp Leu Thr Leu Gly Ala Pro
        370              375              380
Ala Thr Asn Thr Asn Asp Ile Pro Phe Lys Pro Pro Phe Pro Ala Tyr
385              390              395              400
Pro Ser Gly His Ala Thr Phe Gly Gly Ala Val Phe Gln Met Val Arg
            405              410              415
Arg Tyr Tyr Asn Gly Arg Val Gly Thr Trp Lys Asp Asp Glu Pro Asp
        420              425              430
Asn Ile Ala Ile Asp Met Met Ile Ser Glu Glu Leu Asn Gly Val Asn
            435              440              445
Arg Asp Leu Arg Gln Pro Tyr Asp Pro Thr Ala Pro Ile Glu Asp Gln
        450              455              460
Pro Gly Ile Val Arg Thr Arg Ile Val Arg His Phe Asp Ser Ala Trp
465              470              475              480
Glu Leu Met Phe Glu Asn Ala Ile Ser Arg Ile Phe Leu Gly Val His
            485              490              495
Trp Arg Phe Asp Ala Ala Ala Arg Asp Ile Leu Ile Pro Thr Thr
        500              505              510
Thr Lys Asp Val Tyr Ala Val Asp Asn Asn Gly Ala Thr Val Phe Gln
        515              520              525
Asn Val Glu Asp Ile Arg Tyr Thr Thr Arg Gly Thr Arg Glu Asp Pro
530              535              540
Glu Gly Leu Phe Pro Ile Gly Gly Val Pro Leu Gly Ile Glu Ile Ala
545              550              555              560
Asp Glu Ile Phe Asn Asn Gly Leu Lys Pro Thr Pro Glu Ile Gln
            565              570              575
Pro Met Pro Gln Glu Thr Pro Val Gln Lys Pro Val Gly Gln Gln Pro
        580              585              590
Val Lys Gly Met Trp Glu Glu Glu Gln Ala Pro Val Val Lys Glu Ala
            595              600              605
Pro

<210> SEQ ID NO 2
<211> LENGTH: 600
<212> TYPE: PRT
<213> ORGANISM: Curvularia sp.

<400> SEQUENCE: 2

Met Gly Ser Val Thr Pro Ile Pro Leu Pro Thr Ile Asp Glu Pro Glu
1               5                  10                  15
Glu Tyr Asn Asn Asn Tyr Ile Leu Phe Trp Asn Asn Val Gly Leu Glu
                20                  25                  30
Leu Asn Arg Leu Thr His Thr Val Gly Gly Pro Leu Thr Gly Pro Pro
        35                  40                  45
Leu Ser Ala Arg Ala Leu Gly Met Leu His Leu Ala Ile His Asp Ala
    50                  55                  60
Tyr Phe Ser Ile Cys Pro Pro Thr Glu Phe Thr Thr Phe Leu Ser Pro
65                  70                  75                  80
Asp Ala Glu Asn Pro Ala Tyr Arg Leu Pro Ser Pro Asn Gly Ala Asp
                85                  90                  95
Asp Ala Arg Gln Ala Val Ala Gly Ala Ala Leu Lys Met Leu Ser Ser
            100                 105                 110
Leu Tyr Met Lys Pro Ala Asp Pro Asn Thr Gly Thr Asn Ile Ser Asp
```

```
            115                 120                 125
Asn Ala Tyr Ala Gln Leu Ala Leu Val Leu Glu Arg Ala Val Val Lys
    130                 135                 140

Val Pro Gly Gly Val Asp Arg Glu Ser Val Ser Phe Met Phe Gly Glu
145                 150                 155                 160

Ala Val Ala Asp Val Phe Phe Ala Leu Leu Asn Asp Pro Arg Gly Ala
                165                 170                 175

Ser Gln Glu Gly Tyr Gln Pro Thr Pro Gly Arg Tyr Lys Phe Asp Asp
                180                 185                 190

Glu Pro Thr His Pro Val Val Leu Val Pro Val Asp Pro Asn Asn Pro
                195                 200                 205

Asn Gly Pro Lys Met Pro Phe Arg Gln Tyr His Ala Pro Phe Tyr Gly
    210                 215                 220

Met Thr Thr Lys Arg Phe Ala Thr Gln Ser Glu His Ile Leu Ala Asp
225                 230                 235                 240

Pro Pro Gly Leu Arg Ser Asn Ala Asp Glu Thr Ala Glu Tyr Asp Asp
                245                 250                 255

Ser Ile Arg Val Ala Ile Ala Met Gly Gly Ala Gln Asp Leu Asn Ser
                260                 265                 270

Thr Lys Arg Ser Pro Trp Gln Thr Ala Gln Gly Leu Tyr Trp Ala Tyr
    275                 280                 285

Asp Gly Ser Asn Leu Val Gly Thr Pro Pro Arg Phe Tyr Asn Gln Ile
    290                 295                 300

Val Arg Arg Ile Ala Val Thr Tyr Lys Lys Glu Asp Leu Ala Asn
305                 310                 315                 320

Ser Glu Val Asn Asn Ala Asp Phe Ala Arg Leu Phe Ala Leu Val Asn
                325                 330                 335

Val Ala Cys Thr Asp Ala Gly Ile Phe Ser Trp Lys Glu Lys Trp Glu
                340                 345                 350

Phe Glu Phe Trp Arg Pro Leu Ser Gly Val Arg Asp Asp Gly Arg Pro
    355                 360                 365

Asp His Gly Asp Pro Phe Trp Leu Thr Leu Gly Ala Pro Ala Thr Asn
    370                 375                 380

Thr Asn Asp Ile Pro Phe Lys Pro Pro Phe Pro Ala Tyr Pro Ser Gly
385                 390                 395                 400

His Ala Thr Phe Gly Gly Ala Val Phe Gln Met Val Arg Arg Tyr Tyr
                405                 410                 415

Asn Gly Arg Val Gly Thr Trp Lys Asp Asp Glu Pro Asp Asn Ile Ala
                420                 425                 430

Ile Asp Met Met Ile Ser Glu Glu Leu Asn Gly Val Asn Arg Asp Leu
                435                 440                 445

Arg Gln Pro Tyr Asp Pro Thr Ala Pro Ile Glu Asp Gln Pro Gly Ile
    450                 455                 460

Val Arg Thr Arg Ile Val Arg His Phe Asp Ser Ala Trp Glu Met Met
465                 470                 475                 480

Phe Glu Asn Ala Ile Ser Arg Ile Phe Leu Gly Val His Trp Arg Phe
                485                 490                 495

Asp Ala Ala Ala Ala Arg Asp Ile Leu Ile Pro Thr Asn Thr Lys Asp
                500                 505                 510

Val Tyr Ala Val Asp Ser Asn Gly Ala Thr Val Phe Gln Asn Val Glu
                515                 520                 525

Asp Val Arg Tyr Ser Thr Lys Gly Thr Arg Glu Gly Arg Glu Gly Leu
                530                 535                 540
```

Phe Pro Ile Gly Gly Val Pro Leu Gly Ile Glu Ile Ala Asp Glu Ile
545                 550                 555                 560

Phe Asn Asn Gly Leu Arg Pro Thr Pro Pro Glu Leu Gln Pro Met Pro
            565                 570                 575

Gln Asp Thr Pro Val Gln Lys Pro Val Gln Gly Met Trp Asp Glu Gln
        580                 585                 590

Val Pro Leu Val Lys Glu Ala Pro
        595                 600

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
cgcggatcct ctatatacac aactgg                                          26

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
gaagatctcg agttaattaa tcactgg                                         27

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
gaatgacttg gttgacgcgt caccagtcac                                      30

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
ggtctgtatt gggcctacct tgggtcaaac c                                    31

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
ggtctgtatt gggcctacga ggggtcaaac c                                    31

<210> SEQ ID NO 8
<211> LENGTH: 25
<212> TYPE: DNA
<213> ORGANISM: Artificial Sequence
<220> FEATURE:

-continued

```
<223> OTHER INFORMATION: Primer

<400> SEQUENCE: 8
cgccatttct gagatcttcc tgggc                                              25

<210> SEQ ID NO 9
<211> LENGTH: 36
<212> TYPE: DNA
<213> ORGANISM: Artificial Sequence
<220> FEATURE:
<223> OTHER INFORMATION: Primer

<400> SEQUENCE: 9
gcatcttcct cggcagccac tggcgattcg atgccg                                  36
```